United States Patent [19]

Britt et al.

[11] Patent Number: 4,683,333

[45] Date of Patent: Jul. 28, 1987

[54] PROCESS FOR PREPARING SUBSTITUTED BIS-ETHERS

[75] Inventors: Thomas R. Britt, Denham Springs; Willie C. Burton, Baton Rouge, all of La.

[73] Assignee: The Dow Chemical Company, Midland, Mich.

[21] Appl. No.: 800,885

[22] Filed: Nov. 22, 1985

[51] Int. Cl.$^4$ .................. C07C 85/24; C07C 85/00
[52] U.S. Cl. .................. 564/414; 564/306; 564/430; 564/442; 564/443; 568/585; 568/631; 568/635
[58] Field of Search ............. 564/306, 414, 430, 442, 564/443; 568/585, 631, 635

[56] References Cited

U.S. PATENT DOCUMENTS

| | | | |
|---|---|---|---|
| 3,228,982 | 1/1966 | Washburn et al. | 564/414 X |
| 3,338,967 | 8/1967 | Potts et al. | 260/583 |
| 3,592,854 | 7/1971 | Potts et al. | 564/414 X |
| 3,845,225 | 10/1974 | Crosby et al. | 426/217 |
| 3,847,867 | 11/1974 | Heath et al. | 260/47 CP |
| 3,932,360 | 1/1976 | Cerankowski et al. | 260/77.5 AM |
| 4,124,640 | 11/1978 | Shinohara et al. | 564/443 |
| 4,161,474 | 7/1979 | Campbell et al. | 564/443 X |
| 4,231,963 | 11/1980 | Shinohara et al. | 564/443 |
| 4,534,908 | 8/1985 | Fuchs et al. | 564/414 X |
| 4,600,798 | 7/1986 | Cella | 564/443 UX |

OTHER PUBLICATIONS

Thomas R. Britt, "Liquid Crystal Compounds and Related Mesogenic Polymers", Aug. 1981, pp. 58–60, 65–68 and 87, PhD Dissertation.

*Primary Examiner*—Paul F. Shaver
*Attorney, Agent, or Firm*—D. R. Howard

[57] ABSTRACT

Substituted bis-ethers, such as $\alpha,107$ -bis-(4-aminophenoxy)-alkyls, are prepared in process which involves sequential addition of reactants, reagents or neutralizing compounds without recovery of intermediate products such as diamides and diamine acid salts. When water is used as the solvent, the process is simplified and product yields in excess of about 70% are obtained.

23 Claims, No Drawings

PROCESS FOR PREPARING SUBSTITUTED BIS-ETHERS

BACKGROUND OF THE INVENTION

The present invention relates generally to a process for the preparation of substituted bis-ethers. More particularly, the present invention relates to an aqueous process for preparing substituted bis-ethers such as α,ω-bis-(4-aminophenoxy)-alkyls. The substituted bis-ethers are useful as precursors in preparing a variety of polymers or polymer precursors, such as polyimines, polyisocyanates and the like. These polymers and polymer precursors can, in turn, be used in preparing other polymer products such as polyether imides, polyamide-ethers, polyurethanes, polyureas and the like.

Known methods for preparing diamine substituted bis-ethers are generally complex. In fact, one method used to prepare water insoluble diamines of the formula

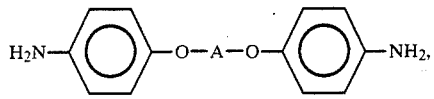

wherein A is a divalent alkyl radical of up to about eighteen carbon atoms, involves seven steps. In a first step, acetamidophenol is added, with stirring, to dimethylformamide to form a mixture. Stirring of the mixture is continued through step three of the method. In step two, potassium carbonate and a dihaloalkane are added to the mixture after the amidophenol dissolves. In a third step, the mixture is heated under a nitrogen purge at reflux for four hours. In a fourth step, stirring is stopped and the mixture is poured into ice water and allowed to stand for several hours to precipitate a diamide. Fifth, the precipitate is filtered, washed with water and dried. Sixth, the diamide precipitate is hydrolyzed with an acid and alcohol mixture to provide a diamine salt. Finally, the diamine salt is isolated and then slurried with a saturated aqueous NaHCO₃ solution to neutralize the salt and yield free diamine.

The aforementioned known process suffers from two primary disadvantages from an industrial process viewpoint. First, the yield is comparatively low—only about fifty percent under optimal conditions. Second, the process is complex and involves at least one intermediate drying step and a final alcohol recovery process. These disadvantages translate to significant cost and equipment constraints which make the process economically unattractive.

A process for preparing diamines with yields in excess of seventy percent, based upon starting materials, would be desirable. A simple, single vessel method wherein intermediate isolation and purification steps are eliminated would also be desirable.

SUMMARY OF THE INVENTION

In one aspect, the present invention is an aqueous process for preparing a water-insoluble, substituted bis-ether of the formula

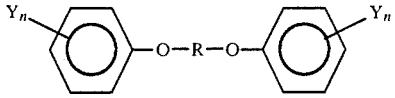

wherein R is a divalent organic radical, Y is a monovalent radical and n is an integer of from about 1 to about 5. R is beneficially a divalent alkyl radical having from about 2 to about 40 carbon atoms, a divalent cycloalkyl radical having from about 3 to about 8 carbon atoms, a divalent bridged ring aliphatic radical having from about 5 to about 10 carbon atoms, a divalent aromatic radical, a divalent alkylaryl radical having from about 7 to about 30 carbon atoms or a divalent fused ring aromatic compound having from about 10 to about 14 carbon atoms. R is suitably a divalent alkyl radical having from about 2 to about 18 carbon atoms, preferably from about 2 to about 10 carbon atoms. Y is beneficially a monovalent radical selected from group consisting of an amino radical, a halogen radical, a hydroxy radical, an alkyl radical of 1 to 30 carbon atoms, an aryl radical of 6 to 14 carbon atoms, a cycloalkyl radical having from 3 to 8 carbon atoms, an alkylaryl radical having from 7 to 30 carbon atoms, a substituted alkylaryl radical, a substituted aryl radical or a substituted cycloalkyl radical.

The process comprises several sequential steps. In a first step, an admixture comprising (1) an organic dihalo compound, (2) an aqueous solution of a phenol which is substituted with at least one halogen-reactive moiety, and (3) an aqueous base solution is refluxed for a period of time sufficient to form an intermediate compound. The admixture may be prepared either in advance or in situ. Refluxing is beneficially conducted under an inert gaseous atmosphere. In a second step, the intermediate compound is hydrolyzed with a mineral acid mineral acid/water solution or a mineral acid/alcohol solution. The hydrolysis step is also beneficially conducted under an inert gaseous atmosphere. In a third step, the hydrolyzed compound is neutralized with a base to provide the substituted bis-ether. The phenol may be further substituted provided such substituents do not substantially interfere with preparation of the bis-ether. The bis-ether is recovered by known methods.

In a second aspect, the present invention is an aqueous process for preparing a water-insoluble diamine of the formula

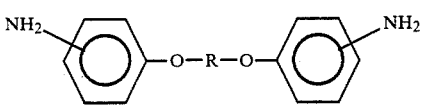

wherein R has the same meaning as above.

The process comprises several steps. In a first step, an admixture comprising (1) an organic dihalo compound, (2) an aqueous solution of an amidophenol, or substituted amidophenol, and (3) an aqueous base solution is refluxed for a period of time sufficient to form an aqueous dispersion of a bis-(4-amidophenoxy)-R compound. Refluxing is beneficially done under an inert atmosphere such as gaseous nitrogen. The amidophenoxy group may be further substituted provided such substituents do not substantially interfere with preparation of the diamine. In a second step, the aqueous dispersion is hydrolyzed with a mineral acid to convert the bis-(4- amidophenoxy)-R compound to its corresponding diamine acid salt. The mineral acid may be in admixture with water or alcohol. In a third step, the diamine acid salt solution is contacted with an amount of an aqueous base solution sufficient to convert the diamine acid salt to its corresponding free diamine. The diamine is insoluble in water and precipitates out of solution. Recovery of the diamine is accomplished by known methods.

DETAILED DESCRIPTION OF THE INVENTION

Substituted phenols suitable for purposes of this invention must have at least one halogen-reactive moiety or group attached thereto. The substituted phenols may have other moieties attached thereto provided such other moieties do not substanlially interfere with preparation of diamines or bis-ethers as disclosed herein. Examples of acceptable halogen-reactive moieties include hydroxy radicals and thiol radicals. The other moieties are beneficially monovalent groups such as alkyl radicals having from 1 to 40 carbon atoms, aryl radicals having 6 to 14 carbon atoms, cycloalkyl radicals having from 3 to 8 carbon atoms, alkylaryl radicals having from 7 to 30 carbon atoms, substituted alkylaryl radicals, substituted aryl radicals, substituted cycloalkyl radicals, ether radicals, imido radicals and amido radicals. The other moieties are desirably alkyl radicals having from 1 to 12 carbon atoms or aryl radicals having from 6 to 10 carbon atoms.

Examples of dihalo compounds useful in this invention include dibromoethane, dibromopropane, dibromobutane, dibromopentane, dibromohexane, dibromoheptane, dibromooctane, dibromononane, dibromodecane, dichloroethane, dichloropropane, dichlorobutane, dichloropentane, dichlorohexane, dichloroheptane, dichlorooctane, dichlorononane, dichlorodecane, diiodoethane, diiodopropane, diiodobutane, diiodopentane, diiodohexane, diiodoheptane, diiodooctane, diiodononane and diiododecane. Other suitable dihalo compounds include those which will react with substituted phenols to provide R, defined hereinabove as a linking group between two substituted ether moieties. The dihalo compounds are beneficially dibromoalkyl compounds wherein the alkyl moiety from about 2 to about 40 carbon atoms. The dihalo compounds are desirably dibromoalkyl compounds wherein the alkyl moiety has from about 2 to about 10 carbon atoms.

The process of the present invention can be conducted at any temperature at which the reaction proceeds. Beneficial results are obtained at temperatures between about 60° Centigrade (hereinafter ° C.) and 100° C. desirable results are obtained at temperatures of from about 80° to about 100° C. Preferred results are obtained at the reflux temperature of water, about 100° C.

The process can be performed at any pressure at which the reaction proceeds, either atmospheric or superatmospheric. Beneficial results are obtained at pressures of from about one to about twenty atmospheres. Desirable results are obtained at pressures of from about one to about ten atmospheres.

Preparation of diamines and substituted bis-ethers is suitably accomplished in the presence of an inert atmosphere such as nitrogen, argon, helium, neon, krypton, xenon, radon or carbon dioxide. For economic reasons, the inert gas is desirably nitrogen. Air can be used rather than an inert gas provided a lower yield is acceptable.

If the dihalo compounds are solid at room temperature and insoluble in water, a phase transfer catalyst (or agent) should be used for two reasons. First, final product yield will be increased over that available in the absence of such a catalyst. Second, reaction time will be much less than that required if such a catalyst is not used.

Phase transfer agents suitable for purposes of the present invention are represented by the general formula

wherein each R' is an alkyl group having from about 1 to about 10 carbon atoms, desirably from about 2 to about 6 carbon atoms, or one R' is an aryl group, such as a benzyl group, N is nitrogen and X is a halogen radical selected from the group consisting of chlorine, bromine and iodine radicals, a hydroxy radical or a hydrogen sulfate radical. Illustrative catalysts include tetrabutylammonium bromide, tetrabutylammonium chloride, tetrabutylammonium iodide, tetrabutylammonium hydroxide, tetrabutylammonium hydrogen sulfate, benzyltrimethylammonium chloride, benzyltriethylammonium chloride and the like. The catalyst is beneficially tetrabutylammonium bromide.

The amount of catalyst may range from about 0.05 to about 2.5 parts per hundred parts of substituted phenol. Amounts of less than about 0.05 parts do not appreciably increase yield or decrease reaction time. Amounts in excess of about 2.5 parts per hundred parts of substituted phenol may be used, but are believed to be economically unattractive.

Suitable reaction times for the reaction of the dihalo compound and the substituted phenol are those which provide a reasonable yield of the desired product. Beneficial results are obtained with reaction times of from about one to about ten hours. Reaction times of greater than ten hours may be necessary when the dihalo compounds are dihaloalkyl compounds wherein the alkyl moiety has more than ten carbon atoms. The reaction time needed for each dihalo compound is readily determined without undue experimentation.

The process of this invention results in surprisingly high yields of desired products. Product yield is dependent upon a number of interrelated factors such as temperature, time, atmosphere, pressure and nature of reactants. One of the reactants, the dihalo compound, plays a major part in determining product yield. It has been found that product yield increases as the halogen changes from chlorine to bromine to iodine. Where the halogen is bromine, as in 1,3-dibromopropane, yields of greater than about 70 percent, based upon moles of dihalo compound added, are obtained.

Preparation of water-insoluble bis-ethers and diamines is highly solvent-dependent. Under identical conditions, save for choice of solvent, product yield using a dibromo compound as one of the reactants varies from a low of about 1-2% with dimethyl formamide, through about 70% or higher with water, to about 80% with hexamethyl phosphoramide.

Notwithstanding potential high yields with hexamethyl phosphoramide, water is the preferred solvent for a number of interrelated reasons. First, the use of water is conducive to a reaction scenario consisting of sequential addition of reactants and neutralizing agents.

Second, diamides formed by reacting an amidophenol and a dihalo compound are insoluble in water, but partially soluble in water/alcohol mixtures. When water/alcohol mixtures are used as the solvent, recovery of the diamides by filtration and drying necessarily leads to some loss of diamide with subsequent lower yield of diamines. In addition, diamides so prepared tend to hold water or other solvents very tenaciously, thereby making the drying thereof both energy intensive and time consuming. In the case of organic solvents such as hexamethyl phosphoramide, complete solvent removal may not be possible. Third, diamine acid salts, an intermediate compound in the preparation of diamines, are generally soluble in water but only sparingly soluble in alcohol or mixtures of alcohol and water having an alcohol content of greater than about 40%. Neutralization of the diamine acid salts to form the free diamine occurs faster in water than in water/alcohol mixtures or in alcohol. In addition, the use of alcohol increases production costs because of its expense and because it must be recovered from the diamine before the latter can be used. In other words, the use of water as the solvent provides the benefits of a simplified, more economical process which gives high product yields.

Enhanced product yields are believed to be attainable in closed reaction systems, particularly when the dihalo compounds have low molecular weights. As the molecular weight of the dihalo compound decreases, its volatility increases. Accordingly, higher yields approaching 90% or even 100% are attainable when the diahlo compound is kept in contact with a substituted phenol rather than being lost to a scrubber, a recovery system or the like.

Skilled artisans recognize that basic compounds, such as those described herein, are highly corrosive. This corrosivity is an important consideration in selecting reactor design and materials of construction.

The following examples are solely for purposes of illustrating the principles of the invention. They are not to be construed as limitations upon the scope of the present invention.

EXAMPLE 1

Preparation of Diamines Using Concentrated HCl to Hydrolyze A Diamide to Its Corresponding Diamine Salt One mole (151.7 grams) of 4-acetamidophenol was suspended in water in a five-liter, three-necked flask provided with a reflux condenser, dropping funnel, mechanical stirrer, and nitrogen inlet. After establishing a nitrogen atmosphere in the flask, one mole (40 grams) of an aqueous sodium hydroxide solution was added, with stirring, to the contents of the flask. The contents were heated, with stirring, to 80°-90° C., whereupon the reaction mixture in the flask turned pink. One-half of a mole (100.9 grams, 50.7 milliliters) of 1,3-dibromopropane was placed in the dropping funnel and slowly added to the flask over a period of one hour while the contents of the flask were stirred. Heating and stirring were continued for an additional four hours, during which an off-white precipitate, or intermediate product, was formed. The precipitate was later identified as 1,3-bis(4-acetamidophenoxy)propane.

The intermediate product was filtered, washed with water and then recrystallized from ethanol. The recrystallized material was suspended in water in the five-liter flask, and treated with 400 milliliters of concentrated hydrochloric acid. The mixture was refluxed for five hours to hydrolyze the amide to the corresponding diamine hydrochloride salt, which remained in solution. The solution was then poured into a cold (about 0° C.) mixture of ice and aqueous sodium hydroxide to liberate the free diamine, 1,3-bis(4-aminophenoxy)propane, in 77 percent yield based on the dibromopropane. The melting point was determined to be 102°-103° C. by differential-scanning calorimetry.

The yield was calculated as the number of moles of the diamine recovered per hundred moles of the dibromopropane charged to the reaction flask. The number of moles of diamine was computed from the weight of diamine recovered. Similar results are obtained with other starting materials detailed herein.

EXAMPLE 2

Synthesis of 1,6-Bis(4-aminophenoxy)hexane Using a Single Reaction Vessel and Avoiding Recovery of Intermediates Twenty grams (0.1323 moles) of 4-acetamidophenol was placed in a 500 milliliter, three-necked flask fitted with a reflux condenser, a dropping funnel and a nitrogen inlet. A stirring bar was placed in the bottom of the flask. A magnetic stirrer was used to actuate the stirring bar. A heating mantle was used to heat the flask and its contents. After adding 100 milliliters of water to the flask, a nitrogen atmosphere was established therein. A solution of 5.3 grams (0.1323 moles) of sodium hydroxide in about 25 milliliters of water was then added to the flask via the dropping funnel.

Following addition of the sodium hydroxide solution, the contents of the flask were heated to reflux. The dropping funnel was used to add 16.1 grams (0.066 moles) of 1,6-dibromohexane dropwise over a period of about one hour. Refluxing was continued for an additional four hours to yield a diacetamide intermediate.

Without recovery of the diacetamide, eighty-five milliliters (about one mole) of 12N hydrochloric acid were added to the flask to hydrolyze the amide groups. The oontents of the flask were stirred and heated at reflux for an additional four hours to complete the hydrolysis and form a transparent, amber-colored solution containing a diamine hydrochloride salt. The heating mantle was then removed, stirring was stopped and the contents of the flask were allowed to cool to room temperature (about 25° C.).

After the contents of the flask cooled to room temperature, aqueous sodium hydroxide was added to the flask to neutralize the acid and liberate the free diamine. The diamine precipitated out of solution. The yield of diamine, calculated as in Example 1, was about 83 percent. The diamine had a melting point, determined as in Example 1, of 150° C.

EXAMPLE 3

Synthesis of 1,10-Bis(4-Aminophenoxy)decane Using a Single Reaction Vessel and Avoiding Recovery of Intermediates The apparatus and procedures detailed in Example 2 were used with some modifications to synthesize 1,10-Bis(aminophenoxy) decane. The modifications were as follows: (1) dibromodecane was used in place of dibromohexane; (2) the reaction mixture was refluxed for ten hours following addition of the dihaloalkane rather than four hours (3) a small amount of a phase transfer catalyst was added to the reaction mixture; and (4) the diamine acid salt did not go into solution as it did in Example 2. Dibromodecane, a solid at 25° Centigrade, was added to the refluxing mixture of water, 4-acetamidophenol and sodium hydroxide solution in two portions, twenty minutes apart. The portions were approximately equal. The total amount of dibromodecane was 19.8 grams (0.066 moles).

Tetrabutylammonium bromide was used as the phase transfer catalyst. It was added to the contents of the flask immediately following addition of the second portion of the 1,10-dibromodecane. The amount of catalyst was 0.50 grams, or 2.5 parts per hundred parts of 4-acetamidophenol.

Diamine yield, determined as in Example 1, was about 81 percent. The melting point of the diamine, determined as in Example 1, of 118° C.

The data presented in Examples 1 through 3 demonstrate the viability of the process of the present invention. Example 1 includes the step of recovering the diacetamide intermediate product via filtration. Examples 2 and 3 show that the recovery step is not needed and that higher yields are attained when the step is omitted. Similar results are obtained when other Bis-ethers are prepared using the process of the present invention and other starting materials which are detailed herein.

What is claimed:

1. An aqueous process for preparing a water insoluble substituted bis-ether of the formula

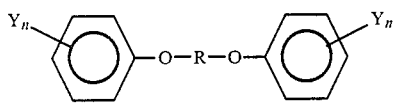

wherein R is a divalent alkyl radical having from about 2 to about 40 carbon atoms, a divalent cycloalkyl radical having from about 3 to about 8 carbon atoms, a divalent bridged ring aliphatic radical having from about 5 to about 10 carbon atoms, a divalent aromatic radical, a divalent alkylaryl radical having from about 7 to about 30 carbon atoms or a divalent fused ring aromatic compound having from about 10 to about 14 carbon atoms; Y is a monovalent radical selected from the group consisting of an amino radical, a halogen radical, a hydroxy radical, an alkyl radical of 1 to 30 carbon atomS, an aryl radical of 6 to 14 carbon atoms, a cycloalkyl radical having from 3 to 8 carbon atoms, an alkylaryl radical having from 7 to 30 carbon atoms, a substituted alkylaryl radical, a substituted aryl radical or a substituted cycloalkyl radical; and n is an integer of from about 1 to about 5 inclusive, which process comprises:

(a) refluxing an admixture comprising (1) an organic dihalo compound, (2) an aqueous solution of a phenol which is substituted with at least one halogen-reactive moiety, and (3) an aqueous base solution, for a period of time sufficient to form an intermediate compound;
(b) hydrolyzing said intermediate compound with a mineral acid; and
(c) neutralizing said hydrolyzed compound with a base to provide the substituted bis-ether.

2. The process of claim 1 wherein R is a divalent alkyl radical having from about 2 to about 18 carbon atoms.

3. The process of claim 1 wherein R is a divalent alkyl radical having from about 2 to about 10 carbon atoms.

4. The process of claim 2 wherein Y is an amino radical.

5. The process of claim 1 wherein steps (a) and (b) are conducted under an inert gaseous atmosphere.

6. The process of claim 5 wherein the inert gaseous atmosphere is provided by at least one gas selected from the group consisting of nitrogen, argon, helium, neon, krypton, xenon, radon or carbon dioxide.

7. The process of claim 6 wherein the gas is nitrogen.

8. The process of claim 1 wherein the organic dihalo compound is selected from the group consisting of dibromoethane, dibromopropane, dibromobutane, dibromopentane, dibromohexane, dibromoheptane, dibromooctane, dibromononane, dibromodecane, dichloroethane, dichloropropane, dichlorobutane, dichloropentane, dichlorohexane, dichloroheptane, dichlorooctane, dichlorononane, dichlorodecane, diiodoethane, diiodopropane, diiodobutane, diiodopentane, diiodohexane, diiodoheptane, diiodooctane, diiodononane and diiododecane.

9. The process of claim 1 wherein the organic dihalo compound is a dibromoalkyl compound, the alkyl moiety thereof having from about 2 to about 40 carbon atoms.

10. The process of claim 9 wherein the alkyl moiety has from about 2 to about 10 carbon atoms.

11. The process of claim 1 wherein the phenol is also substituted with at least one monovalent group selected from the group consisting of alkyl radicals having from 1 to 40 carbon atoms, aryl radicals having 6 to 14 carbon atoms, cycloalkyl radicals having from 3 to 8 carbon atoms, alkylaryl radicals having from 7 to 30 carbon atoms, substituted alkylaryl radicals, substituted aryl radicals, substituted cycloalkyl radicals, ether radicals, imido radicals and amido radicals.

12. The process of claim 11 wherein the monovalent group is an alkyl radical having from 1 to 12 carbon atoms or an aryl radical having from 6 to 10 carbon atoms.

13. An aqueous process for preparing a water-insoluble diamine of the formula

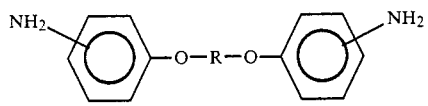

wherein R is a divalent alkyl radical having from about 2 to about 40 carbon atoms, a divalent cycloalkyl radical having from about 3 to about 8 carbon atoms, a divalent bridged ring aliphatic radical having from about 5 to about 10 carbon atoms, a divalent aromatic radical, a divalent alkylaryl radical having from about 7 to about 30 carbon atoms or a divalent fused ring aromatic compound having from about 10 to about 14 carbon atoms which comprises, (a) refluxing an admixture comprising (1) an organic dihalo compound, (2) an aqueous solution of an amidophenol, and (3) an aqueous base solution for a period of time sufficient to form an aqueous dispersion of a bis-(4-amidophenoxy)-R compound;
(b) hydrolyzing the aqueous dispersion with a mineral acid to convert the bis-(4-amidophenoxy)-R compound to its corresponding diamine acid salt; and
(c) contacting the diamine acid salt solution with sufficient aqueous base solution to convert said diamine acid salt to its corresponding free diamine.

14. The process of claim 13 wherein R is a divalent alkyl radical having from about 1 to about 18 carbon atoms.

15. The process of claim 13 wherein R is a divalent alkyl radical having from about 1 to about 10 carbon atoms.

16. The process of claim 13 wherein the organic dihalo compound is selected from the group consisting of dibromoethane, dibromopropane, dibromobutane, dibromopentane, dibromohexane, dibromoheptane, dibromooctane, dibromononane, dibromodecane, dichloroethane, dichloropropane, dichlorobutane, dichloropentane, dichlorohexane, dichloroheptane, dichlorooctane, dichlorononane, dichlorodecane, diiodoethane, diiodopropane, diiodobutane, diiodopentane, diiodohexane, diiodoheptane, diiodooctane, diiodononane and diiododecane.

17. The process of claim 13 wherein the organic dihalo compound is a dibromoalkyl compound, the alkyl moiety thereof having up to about 40 carbon atoms.

18. The process of claim 17 wherein the alkyl moiety has from about 1 to about 10 carbon atoms.

19. The process of claim 13 wherein the amidophenol is also substituted with at least one monovalent group selected from the group consisting of alkyl radicals having from 1 to 40 carbon atoms, aryl radicals having 6 to 14 carbon atoms, cycloalkyl radicals having from 3 to 8 carbon atoms, alkylaryl radicals having from 7 to 30 carbon atoms, substituted alkylaryl radicals, substituted aryl radicals, substituted cycloalkyl radicals, ether radicals, imido radicals and amido radicals.

20. The process of claim 19 wherein the monovalent group is an alkyl radical having from 1 to 12 carbon atoms or an aryl radical having from 6 to 10 carbon atoms.

21. The process of claim 13 wherein steps (a) and (b) are conducted under an inert gaseous atmosphere.

22. The process of claim 21 wherein the inert gaseous atmosphere is provided by at least one gas selected from the group consisting of nitrogen, argon, helium, neon, krypton, xenon, radon or carbon dioxide.

23. The process of claim 22 wherein the gas is nitrogen.

* * * * *